United States Patent [19]

Verma

[11] Patent Number: 5,116,758

[45] Date of Patent: May 26, 1992

[54] FERMENTATION VESSEL CLOSURE

[76] Inventor: Kuldeep Verma, 15611 Southland Blvd., Apt. 9, Taylor, Mich. 48180

[21] Appl. No.: 458,990

[22] Filed: Dec. 29, 1989

[51] Int. Cl.[5] .................................. C12M 61/00
[52] U.S. Cl. ................................ 435/287; 215/322; 220/336; 220/345; 435/296; 435/298
[58] Field of Search .............. 435/243, 284, 287, 290, 435/296, 298, 313, 314; 220/336, 345; 215/322

[56] References Cited

U.S. PATENT DOCUMENTS 3,352,445  7/1966  Cochin .............................. 220/336
3,527,373  9/1970  Giraudet et al. .................. 220/345
3,792,803  2/1974  Kessler ............................. 220/345

Primary Examiner—David L. Lacey
Assistant Examiner—Thomas E. Daley
Attorney, Agent, or Firm—Jerry F. Janssen

[57] ABSTRACT

A closure device for fermentation test tubes or flasks comprises a cylindrical cap which fits snugly over the mouth and neck of a test tube or flask to maintain the sterility of the tube or flask contents while permitting the free flow of gases into and out of the tube or flask. An aperture in the end cap of the closure device permits free access to the tube or flask contents for sampling and is closed by a moveable aperture cover.

6 Claims, 2 Drawing Sheets

FERMENTATION VESSEL CLOSURE

BACKGROUND OF THE INVENTION

The present invention relates to closure devices. More particularly, the present invention concerns a closure device for fermentation vessels which permits access to the vessel Fermentation processes are employed for a wide variety of commercially important products ranging from food products to pharmaceuticals. Often in the development of a fermentation process, new strains of microorganisms are isolated and identified which improve a known process or produce a new and useful fermentation product. The isolation of pure strains of microorganisms is a detailed process which involves many steps. Typically, a newly identified colony of a microorganism is first transferred from a Petri dish culture to a test tube containing appropriate nutrients. This culture is often transferred one or more times to new culture tubes until the culture is free of contamination by other undesired strains of microorganisms. These transfers are typically effected by means of a transfer loop which is inserted into the mouth of the culture tube after removing the culture tube closure. Good laboratory practice dictates that both the mouth of the culture tube and the closure be sterilized by flaming prior to replacing the closure on the tube.

Once a pure strain of the desired microorganism has been prepared in a test tube, the culture is typically transferred to a closed shake flask containing a sterile liquid culture medium. The medium is inoculated with the microorganism and placed on a shaking table in an incubator at a temperature and for a period of time sufficient to permit growth of the microorganism culture. During this stage of the process, it is frequently necessary to add materials to the culture medium or to remove aliquot samples from the shake flask for analysis. As before, good laboratory practice requires flame sterilization of the flask mouth and closure before reclosing the flask after each such access to the flask contents. All of these operations require two-hand manipulation of the flask, the closure, and a transfer loop or pipette which can be cumbersome. Moreover, the recent widespread introduction of plastic disposable shake flasks has complicated the step of flame sterilization.

The vast majority of microorganisms useful in commercially viable fermentation processes belong to the class of aerobic microorganisms; that is, microorganisms which require oxygen to carry on their metabolic processes. In fact, the very purpose of shaking or stirring fermentation broths is to ensure effective mixing of air with the liquid culture medium. As a result, any closure device employed in the culturing of aerobic microorganisms must permit the passage of air into the vessel and the exchange of gaseous fermentation products out of the vessel while maintaining the sterility of the vessel contents.

In the past it has been the widespread practice to close fermentation test tubes, flasks, shake flasks, and other small laboratory scale fermentation vessels with a porous closure such as a plug of sterile cotton or similar porous material made of a synthetic material such as foamed polyethylene or polypropylene. More recently stainless steel and plastic cap closures have become available which fit over the mouth of the fermentation test tube or flask, permitting the passage of gases into and out of the fermentation vessel. Examples of such closures are KIM-KAP TM closures, available from Owens-IL, and KAP-UTS TM plastic closures and BELLCO stainless steel closures available from Bellco Technology, P.O. Box 340, Erudo Road, Vineland, NJ 08360. These closures are of a diameter slightly larger than the neck of the fermentation tube or flask and fit snugly over the mouth of the test tube or flask by means of fingers or ridges on the inside vertical walls of the closures. Small stand-offs inside the the closures prevent the seating of the top of the closure against the top of the fermentation tube or flask, thus permitting the passage of gases into and out of the tube while maintaining the sterility of the vessel contents.

A disadvantage of these prior art closures, whether of the porous plug type or the snug-fitting cap closure type, is the need to remove the plug or closure each time access to the fermentation vessel contents is required. Each removal of the closure provides the potential for contamination of the vessel contents and requires flaming of the vessel mouth and closure to ensure sterility.

Thus there is a need in the fermentation art for a closure device which permits direct access to fermentation vessel contents without the need to remove the closure device.

SUMMARY OF THE INVENTION

The present invention provides closure devices for laboratory scale fermentation vessels which permit access to the contents of the vessel without removal of the closure while simultaneously permitting the passage of gases into and out of the vessel and maintaining the sterility of the contents. The closure devices of this invention comprise a cylindrical wall portion open at one end and having at the other end thereof a capping end. Means for engaging the mouth of a fermentation tube or flask are disposed along the inner surface of the cylindrical wall portion and stand-off means for permitting the free flow of gases into and out of the capped fermentation vessel are disposed radially around the inner surface of capping end.

The improvement in the fermentation vessel closures of the present invention comprise an aperture in the capping end with a moveable aperture closure means to permit free access to the fermentation vessel without removal of the closure device.

DETAILED DESCRIPTION

The fermentation test tube or flask closure device of the present invention permit the covering of such fermentation vessels to maintain the sterility of the contents (once sterilized) while permitting the free and easy access to the contents to add to or subtract from the vessel contents. The closure device of this invention may be molded by conventional techniques well known in the molding arts of any suitable flexible material which is capable of withstanding the temperatures required for autoclave sterilization. Suitable materials include polyethylene, polypropylene, high density polyethylene, high density polypropylene, Poly(tetrafluoroethylene), polycarbonates, polystyrene, rubber, and the like.

The closure devices of the present invention have an opening in the top which permits transfer loops, pipettes and the like to be inserted into the fermentation vessel without the removal of the closure device. In one embodiment of the closure device of this invention, depicted in FIGS. 2 and 5, a moveable cover slides laterally in a channel formed in the top of the closure device to expose or to cover an aperture or opening through which transfer loops or pipettes may be inserted into the fermentation test tube or flask. The moveable cover is retained in the channel by means of grooves formed in the side walls of the channel with corresponding tongues on the side walls of the moveable cover. Alternatively, the grooves may be formed in the side walls of the moveable cover with the corresponding tongues formed in the side walls of the channel.

Figure 6:
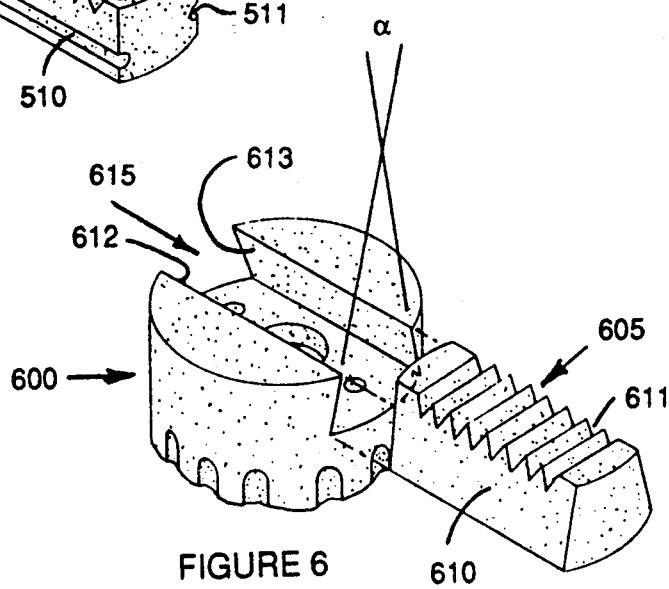
FIG. 6 is a perspective view of a part of a closure device of one embodiment of the present invention.

In another embodiment of the closure device of the present invention, shown in FIG. 6, the side walls of the channel slope inwardly toward one another, with the side walls one another. The movable aperture cover is thus retained in the channel and slides laterally to cover or uncover the aperture or opening in the capping end of the closure device.

To prevent the moveable aperture cover from inadvertently being completely slide out of the channel, one or more detents may optionally be provided on the floor of the channel with correspondingly spaced nipples on the bottom surface of the moveable aperture cover, or vice versa. Preferably, a detent is placed on either side of the aperture or opening in the floor of the channel, spaced apart from the aperture. When the moveable aperture cover is in place, the first nipple engages the first detent and the second nipple engages the second detent. The moveable aperture cover may be slid laterally in either direction to expose the aperture in the floor of the channel, with the first nipple engaging the second detent or vice versa, arresting the lateral movement of the cover, thus preventing the inadvertent movement of the aperture cover completely out of the channel.

Figure 7:
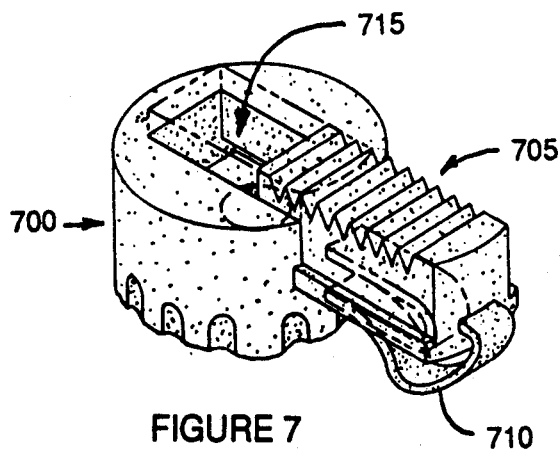
FIG. 7 is a perspective view of a part of a closure device of one embodiment of the present invention.

In another embodiment of the present invention, shown in FIG. 7, the moveable aperture cover may be tied to the body of the closure device by a tether. In this embodiment, the channel is shown being open at one end only, although the channel may extend across the full diameter of the main body portion of the closure device as shown in the embodiments pictured in FIGS. 2, 5, and 6. The moveable aperture cover, tether, and main body portion of the closure device are preferably molded of one piece. In this embodiment, the moveable aperture cover may have either tongue-and-groove arrangement shown in the embodiments depicted in FIGS. 2 or 5. Once the moveable aperture cover is inserted into the channel in the main body portion of the closure device, the tether prevents the cover from being slid completely out of the channel and only a single detent and nipple is needed in the floor of the channel. Moreover, the natural resiliency of the tether serves to restore the moveable aperture cover in its closed position in the channel.

Figure 4:
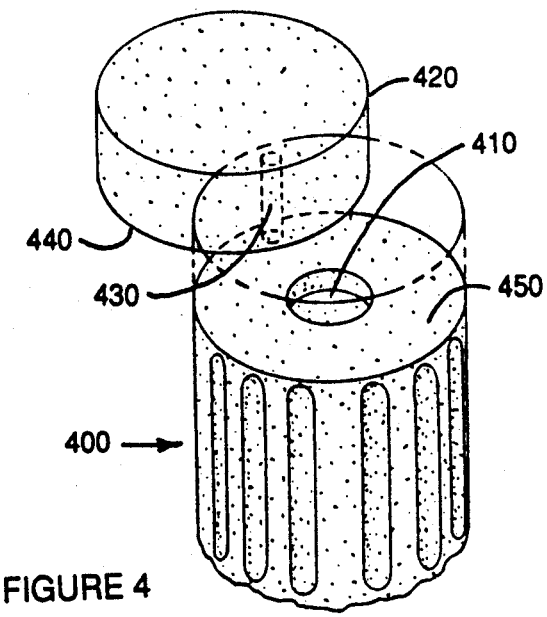
FIG. 4 is a perspective view of a part of a closure device of one embodiment of the present invention.

In another embodiment of the closure device of the present invention, shown in FIG. 4, the aperture closure comprises a rotatable disk, preferably of the same diameter as the body portion of the closure device, having a hinging means disposed off center of the top or capping end of the closure device to permit rotation of the cap to cover or uncover the aperture in the capping end.

Figure 8:
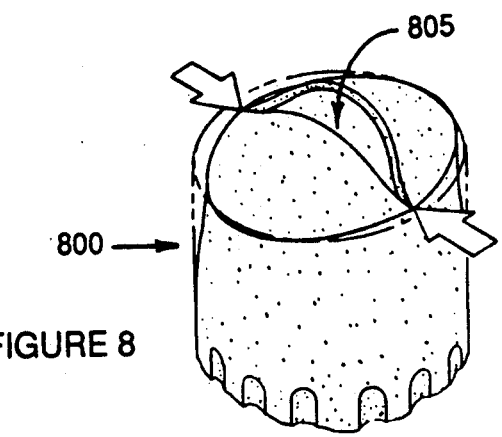
FIG. 8 is a perspective view of a part of a closure device of one embodiment of the present invention.

In another embodiment of the closure device of the present invention, shown in FIG. 8, the closure is formed from a suitable flexible material such as rubber and has a slit running across a diameter of the top or capping end of the closure. The top of the closure device thus comprises a pinch valve; pinching the top of the closure at both ends of the slit (as shown by the heavy arrows in FIG. 8) distorts the slit to form an opening through which transfer loops, pipettes and the like may be inserted into the fermentation vessel.

The closure devices of the present invention provide the convenience to the user of being able to grip the neck of a fermentation test tube or flask and open the closure to carry out sampling or addition operations with one hand, leaving the other hand free for handling a transfer loop or pipette. This obviates the sometimes cumbersome procedure of having to remove the closure entirely to access the vessel contents. The opening of fermentation vessels fitted with closures of the present invention is performed quickly and easily, considerably minimizing the possibility of contaminating the vessel contents. Moreover, the procedure of flame sterilization of the closure and mouth of the fermentation vessel following each opening of the vessel is eliminated with closures of this invention.

Figure 1:
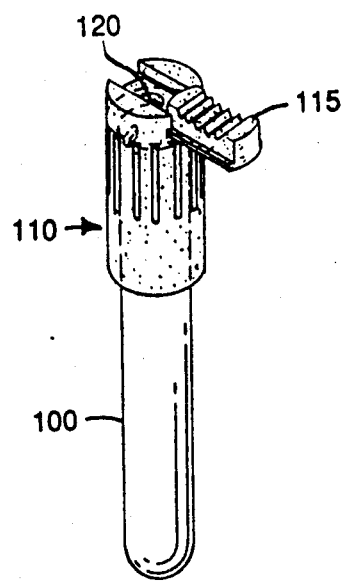
FIG. 1 is a perspective view of a fermentation test tube closed with a closure device in accordance with one embodiment of the present invention.

Referring to FIG. 1, there is shown a fermentation tube 100 closed with a closure device 110 in accordance with one embodiment of the present invention. In FIG. 1, the moveable closure cover 115 is shown in the open position, uncovering the aperture or opening 120 in top end or capping end of the closure device.

Figure 2:
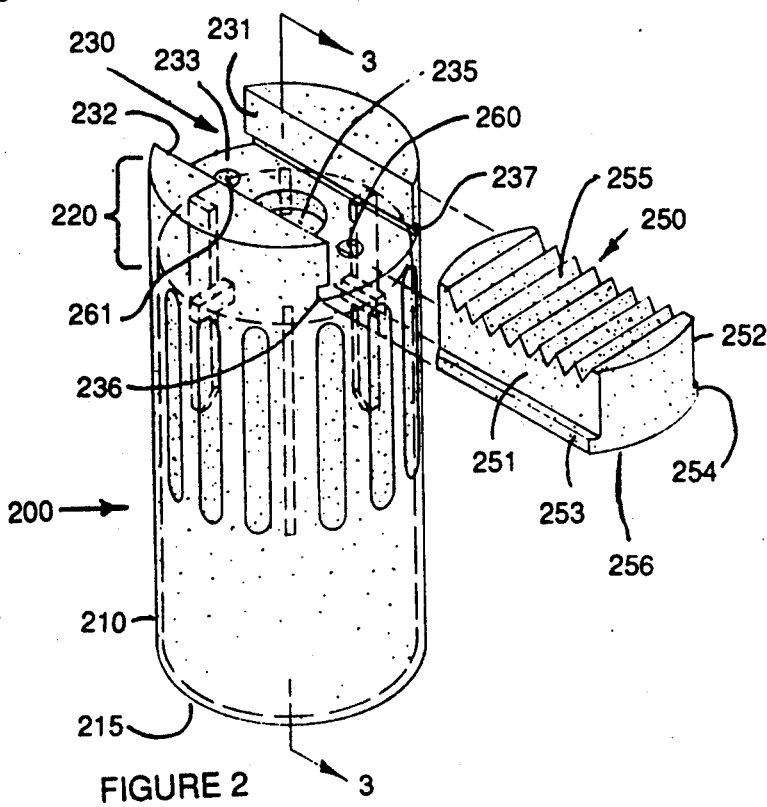
FIG. 2 is an exploded perspective view of a fermentation vessel closure device in accordance with one embodiment of the present invention.

Referring to FIG. 2, the closure device, 200, of this embodiment of the invention is shown in transparent perspective view and comprises a right circular cylinder with vertical cylindrical wall portion, 210, open at one end, 215, to receive the mouth and neck of a fermentation tube or flask, and closed at the opposite end by a top end or capping end, 220. The capping end, 220, of the closure device, 200, has a channel, 230, disposed diametrically across the top of closure device with parallel spaced apart side walls, 231 and 232, and channel bottom surface, 233. An access opening or aperture, 235, is disposed, preferably centrally, in the bottom surface 233 of the channel 230. Indented grooves 236 and 237 are disposed in side walls 231 and 232 of channel 230, the bottom surface 233 of the channel 230 being preferably flush with the bottom of grooves 236 and 237.

Figure 3:
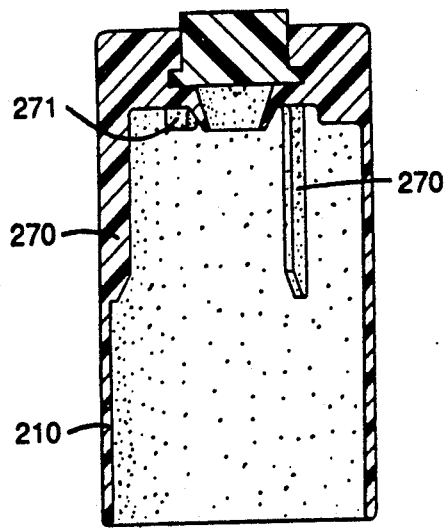
FIG. 3 is a vertical cross-sectional view of the closure device of FIG. 2 taken along the line 3—3.

Moveable closure cover 250 has parallel spaced apart side walls 251 and 252 with tongues 253 and 254, respectively, running along the length of the side walls 25 and 252. Closure cover 250 is adapted to be slideably received in channel 230 with tongues 253 and 254 being slideably received in grooves 236 and 237. The upper surface, 255, of the moveable closure cover 250 may optionally be serrated as shown in FIG. 2 or otherwise suitably roughened to enhance gripping. The bottom surface 233 of channel 230 has two detents, 260 and 261, spaced apart on either side of the aperture or opening, 235, with two nipples correspondingly spaced apart on the bottom surface 256 of the moveable aperture cover 250. One nipple, 262, can be seen in the cross-section shown in FIG. 3.

When the moveable closure cover 250 is fully inserted into channel 230 the nipples are received into the detents, holding the moveable closure cover 250 in place. When the moveable closure cover 250 is slid laterally in one direction in channel 230, the nipple which normally engages detent 260, engages detent 261, or vice versa if the movement of the aperture cover is in the opposite direction.

The inner surface of vertical cylindrical wall 210 of the closure has gripping means for engaging the outer surface of the neck of a fermentation test tube or flask. In a preferred arrangement, the gripping means comprise at least three protrusions 270 which preferably run parallel to the central axis of the closure device and which are spaced apart about the inner surface of the cylindrical wall 210 of the closure device. The protrusions 270 slideably engage the neck of a fermentation tube or flask when the closure device is fitted over the mouth of a test tube or flask. Two of the protrusions can be seen in the cross section shown in FIG. 3.

One or more stand-offs 271 are disposed radially around the inner surface of the top or capping end 220 of the closure. The stand-offs 271 prevent the seating of the inner surface of the capping end of the closure against the mouth of the test tube or flask, thus permitting the free flow of gases into and out of the tube or flask.

A perspective view of a portion of an alternative embodiment of the closure device of the present invention is shown in FIG. 4. In FIG. 4, the closure device 400 has an aperture or opening 410, preferably disposed centrally, in the capping end of the closure. A rotatably hinged aperture closure 420, preferably of a diameter equal to that of the main body portion of the closure device, is attached to the main body portion by means of a hinging pin 430, disposed off-center of the main body portion of the closure. The bottom surface 440 of the aperture closure 420 is flush with the top surface 450 of the main body portion of the closure device. The remaining features of the embodiment shown in FIG. 4, comprising the gripping means disposed on the inner surface of the cylindrical wall portion of the main body of the closure and the stand-off means are as shown in FIG. 2.

Figure 5:
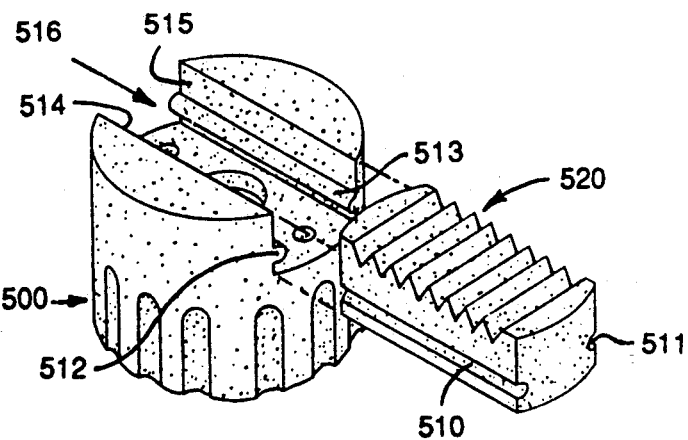
FIG. 5 is a perspective view of a part of a closure device of one embodiment of the present invention.

The embodiment of the closure device 500 shown in FIG. 5 is similar in every respect to that shown in FIG. 2 with the exception that in FIG. 5, grooves 510 and 511 are disposed in the side walls of the moveable aperture cover 520, with corresponding tongues 512 and 513 extending along the side walls 514 and 515 of channel 516.

The embodiment of the closure device 600 shown in FIG. 6 is similar in every respect to that shown in FIG. 2 with the exception that in FIG. 6, the side walls 610 and 611 of the moveable aperture cover 605 do not have tongues but are sloped inwardly toward one another at a dihedral angle α in such a manner that bottom edges of the sidewalls 610 and 611 are further apart than the upper edges of the sidwalls 610 and 611. The sidewall 612 and 613 of channel 615 are similarly s toward one another at the same angle α so that the moveable aperture cover 605 is adapted to be slideably received and retained in channel 615.

The embodiment of the closure device 700 shown in FIG. 7 is similar in every respect to that shown in FIG. 2 with the exception that in FIG. 7, the moveable aperture cover 705 is tethered to the main body portion of the closure device 700 by means of tether strap 710. Although channel 715 may extend all of the way across the top of the closure device as shown in FIG. 2, in this embodiment of the present invention, it is preferred that the channel be closed at one end as shown in FIG. 7.

Yet another embodiment of the closure device of the present invention is depicted in FIG. 8. Referring to FIG. 8, the closure device 800 is comprise of one-piece molded flexible material, preferably rubber or similar elastomeric material. Only the top portion of the closure device is shown, with the remaining structure and features of the closure being similar to that shown in FIG. 2.

The closure device 800 has a slit 805 running, preferably diametrically across the top or capping end of the closure which provides an aperture or opening to access the contents of a tube or flask which is capped with the closure. Pinching the closure with, for example, the thumb and forefinger at the opposite ends of the slit deforms the closure to provide access to the tube or flask contents. In FIG. 8, the closure is depicted in the deformed position, with the normal shape being depicted by dotted lines.

While there have been shown and described what are considered to be the preferred embodiments of the present invention, it will be clear to one skilled in the art that various changes or modifications can be made thereto without departing from the scope of the invention as defined by the appended claims.

I claim:
1. A fermentation vessel closure device comprising
 a cylindrical wall portion open at one end and having at the other end thereof a capping end;
 means for engaging the mouth of a fermentation vessel disposed on the inner surface of said cylindrical wall portion;
 stand-off means disposed on the inner surfaces of said cylindrical wall portion and said capping end to permit the free flow gases into and out of the fermentation vessel;
 a channel with spaced-apart sidewalls and a bottom surface thereof, said channel being disposed diametrically in said capping end;
 an aperture in the bottom surface of said channel;
 a moveable aperture cover being slideably received in said channel; and
 means for retaining said aperture cover in said channel comprising corresponding tongue-and-groove means disposed in the sidewalls of said channel and in the sidewalls of said moveable aperture cover.

2. A fermentation vessel closure device comprising
 a cylindrical wall portion open at one end and having at the other end thereof a capping end;
 means for engaging the mouth of a fermentation vessel disposed alogn the inner surface of said cylindrical wall portion;
 stand-off means disposed on the inner surfaces of said cylindrical wall portion and said capping end for permitting the free flow gases into and out of the fermentation vessel;

a channel disposed diametrically in the capping end of said closure device, said channel having spaced-apart sidewalls and a bottom surface thereof;

an aperture in said bottom surface of said channel to permit access to the contents of the vessel;

said sidewalls of said channel being inwardly sloped toward one another at a dihedral angle α, said sidewalls being further apart at the bottom edges thereof than at the top edges thereof;

a moveable aperture cover having space-apart sidewalls and being slideably received in said channel;

said sidewalls of said moveable aperture cover being inwardly sloped toward one another at said dihedral angle α;

said moveable aperture cover being slideably received and retained in said channel.

3. A fermentation vessel closure device as defined by claim 1 further comprising tethering means for tethering said moveable aperture cover to said capping end of the closure device.

4. A fermentation vessel closure device as defined by claim 2 further comprising tethering means for tethering said movable aperture closing means to the ma body portion of the closure device.

5. A fermentation vessel closure device comprising a cylindrical wall portion open at one end thereof and having at the other end thereof a capping end;

means for engaging the mouth of a fermentation vessel disposed along the inner surfaces of said cylclindrical wall portion and said capping end to permit the free flow of gases into and out of the fermentation vessel;

an aperture in said capping end to permit access to the contents of the fermentation vessel; and moveable means for closing said aperture;

wherein said moveable means for closing said aperture comprises a pinch valve.

6. A fermentation vessel closure as defined by claim 5 further comprising stand-off means disposed on the inner surface of said capping end for permitting the free flow of gases into and out of the fermentation vessel;

said aperture being a slit disposed diametrically across said capping end;

said closure device being fabricated of a flexible material whereby application of pressure to both ends of said slit distorts said closure device forming said aperture to permit access to the fermentation vessel.

* * * * *